United States Patent
Roberts (10) Patent No.: US 11,320,558 B2
(45) Date of Patent: May 3, 2022

(54) APPARATUS FOR MEASURING WIDEBAND DIELECTRIC MEASUREMENTS OF OBJECTS USING A BISTATIC ANTENNA

(71) Applicant: Geophysical Survey Systems, Inc., Nashua, NH (US)

(72) Inventor: Roger Roberts, Amesbury, MA (US)

(73) Assignee: GEOPHYSICAL SURVEY SYSTEMS, INC., Nashua, NH (US)

( * ) Notice: Subject to any disclaimer, the term of this patent is extended or adjusted under 35 U.S.C. 154(b) by 403 days.

(21) Appl. No.: 16/694,159

(22) Filed: Nov. 25, 2019

(65) Prior Publication Data

US 2020/0191989 A1 Jun. 18, 2020

Related U.S. Application Data

(60) Provisional application No. 62/779,555, filed on Dec. 14, 2018.

(51) Int. Cl.

| | |
|---|---|
| *G01R 27/26* | (2006.01) |
| *G01V 3/12* | (2006.01) |
| *G01N 33/42* | (2006.01) |
| *G01N 22/00* | (2006.01) |
| *G01S 13/88* | (2006.01) |
| *G01N 27/22* | (2006.01) |

(52) U.S. Cl.
CPC ............... *G01V 3/12* (2013.01); *G01N 22/00* (2013.01); *G01N 27/22* (2013.01); *G01N 27/221* (2013.01); *G01N 27/223* (2013.01); *G01N 27/226* (2013.01); *G01N 33/42* (2013.01); *G01R 27/26* (2013.01); *G01R 27/2605* (2013.01); *G01S 13/885* (2013.01); *G01R 27/2641* (2013.01)

(58) Field of Classification Search
CPC .......... G01V 3/12; G01N 22/00; G01N 33/42; G01N 27/221; G01N 27/226; G01N 27/223; G01N 27/22; G01S 13/885; G01R 27/2605; G01R 27/26; G01R 27/2641; G01R 27/2623
USPC ........... 324/76.11–76.83, 459, 649, 658, 663
See application file for complete search history.

(56) References Cited

U.S. PATENT DOCUMENTS

| | | | |
|---|---|---|---|
| 10,938,099 B1* | 3/2021 | Roberts | G01S 13/885 |
| 2002/0075006 A1* | 6/2002 | Goldfine | G01R 27/2623 |
| | | | 324/457 |
| 2013/0024150 A1* | 1/2013 | Erb | G01N 23/02 |
| | | | 702/76 |

OTHER PUBLICATIONS

Agilent Technologies, Agilent Basics of Measuring the Dielectric Properties of Materials: Application Note, Jun. 26, 2006, #5989-2589EN [Date accessed May 2, 2019].

(Continued)

*Primary Examiner* — Raul J Rios Russo
(74) *Attorney, Agent, or Firm* — Michael J. Feigin, Esq.; Feigin and Fridman LLC (57) ABSTRACT

A device implementing antennas transmitting and receiving electromagnetic waves for measuring the bulk dielectric properties of a material under test having over a pre-defined surface area. The sample of the material under test might be cylindrical in shape. The device includes a spacer of known dielectric properties and geometries, placed between the material under test and the transmitting and receiving antennas, as well as at least one plate of a material having known electromagnetic properties placed below the material under test.

20 Claims, 7 Drawing Sheets

(56) References Cited

OTHER PUBLICATIONS

Shimizu, Takashi. "Cut-Off Circular Waveguide Method for Dielectric Substrate Measurements in Millimeter Wave Range." IEICE Trans. Electron. vol. E87-C, No. 5, May 2004: pp. 672-680 [Date accessed Mar. 28, 2018].

Gunasekaran, S. et al. "Dielectric Studies of Some Rubber Materials at Microwave Frequencies." Indian Journal of Pure & Applied Physics, vol. 46, Oct. 2008: pp. 733-737 [Date accessed Apr. 19, 2018].

Venkatesh, M.S. et al. "An Overview of Dielectric Properties Measuring Techniques." Canadian Biosystems Engineering, vol. 47, 2005: pp. 7.15-7.30 [Date accessed Mar. 28, 2018].

Cravey, Robin L et al. Dielectric Property Measurements in the Electromagnetic Properties Measurements Laboratory. NASA Technical Memorandum 110147, Langley Research Center, Hampton, VA, Apr. 1995 [Date accessed May 2, 2018].

MD. Maniruzzaman, B. A. Aziz et al. "Preliminary Determination of Asphalt Properties Using Microwave Techniques." ARPN Journal of Engineering and Applied Sciences, vol. 5, No. 11, Nov. 2010: pp. 70-80 [Date accessed Mar. 28, 2018].

Filali, Bilal et al. "Design and Calibration of a Large Open-Ended Coaxial Probe for the Measurement of the Dielectric Properties of Concrete." IEEE Transactions on Microwave Theory and Techniques, vol. 56, No. 10, Oct. 2008: pp. 2322-2328 [Date accessed May 2, 2018].

Gaoyuan-Ci et al. "Waveguide Method for Measuring Dielectric Constant of Asphalt Concrete at 2.45GHz." Proceedings of the 7th WSEAS International Conference on Systems Theory and Scientific Computation, Athens, GA, Aug. 24-26, 2007: pp. 291-293 [Date accessed Mar. 26, 2018].

Cravey, Robin L. et al. Dielectric Property Measurements in the Electromagnetic Properties Measurements Laboratory (Notes on dielectric measurements using waveguides NASA 1995). NASA Technical Memorandum 110147, Langley Research Center, Hampton, VA, Apr. 1995 [Date accessed Mar. 28, 2018].

* cited by examiner

APPARATUS FOR MEASURING WIDEBAND DIELECTRIC MEASUREMENTS OF OBJECTS USING A BISTATIC ANTENNA

FIELD OF THE DISCLOSED TECHNOLOGY

The disclosed technology relates generally to an apparatus and method for calculating the dielectric of a medium, and, more specifically, to an apparatus and method for making wide-band real-time bulk dielectric and/or bottom surface dielectric measurements of media using a bistatic antenna.

BACKGROUND OF THE DISCLOSED TECHNOLOGY

The measurement of dielectric is a straight-forward process when performed using waveguide methods (Tonn, David A., U.S. Pat. No. 7,288,944) or Microwave Free-Space methods (Aziz, Md. Maniruzzaman B. A., et, al, 2010, ARPN Journal of Engineering and Applied Sciences, v. 5, no 11). These methods, however, are limited in their applicability to usage in controlled environments, such as laboratories, and require samples with very specific geometries. Therefore, such methods cannot measure the localized dielectric of large surfaces having varying dielectric properties.

Another method of measuring dielectric is using an open-ended coaxial probe. Such a probe is portable, but has a different set of limitations. The coaxial probe requires good contact with the medium under test, and the medium surface must be at least as flat as the probe face. Additionally, the sample thickness must be sufficient so that the sample appears infinite to the probe. Furthermore, there are accuracy limitations to this method, which has an accuracy of about 5% according to NASA Technical Memorandum 110147.

Another method for measuring the dielectric of a medium in situ, which is increasingly popular, is ground penetrating radar (GPR). This method has been applied for decades to accurately measure the surface dielectric of asphalt using non-contact horn antennas, which are typically mounted on vehicles.

More recently, smaller-size dipole-type antennas have been used to measure the dielectric of asphalt to a higher degree of accuracy. These dipole-type antennas have been used in a non-contact manner similar to the aforementioned horn antennas. In use, such dipole-type antennas are mounted 6 to 12 inches above the asphalt surface, for example on a vehicle, thereby illuminating an area approximately 6" in diameter, while being sensitive to edge diffractions from large dielectric discontinuities over a greater diameter.

Measurement of the dielectric of cores, varying in thickness from 0.5 inches to greater than 6 inches, and of asphalt cylinders manufactured by gyratory compactors, in near real-time, is especially important to industries that rely on calibrating dielectric measurements to variations in asphalt compaction using cores or manufactured cylinders.

Thus, there is a need in the industry for a device and/or a method for quickly and accurately measuring the dielectric of cores and manufactured asphalt specimens that may be, for example, approximately 6" in diameter, such as the bulk dielectric and the bottom dielectric of a small-area sample.

SUMMARY OF THE DISCLOSED TECHNOLOGY

The present disclosure relates to a method, system, and kit for accurately measuring the wideband bulk dielectric and/or bottom surface dielectric of a small-area sample.

A measurement apparatus as disclosed herein includes transmitting and receiving antennas operating over a band of frequencies. The antennas are separated by a distance calibrated to minimize the energy directly passing between the antennas, and to maximize the horizontal resolution of the transmitted energy. The antenna and/or antenna construct may further include a standard Ground Penetrating Radar (GPR) antenna pair, typically intended to be used in close proximity to a surface, such as concrete, for the purpose of detecting rebar.

The measurement apparatus may further include a medium of known electromagnetic properties and dimensions separating the antennas from a surface of the Material Under Test (MUT) whose dielectric properties are being measured. Electromagnetic properties is defined as "properties of a material that modify the electromagnetic fields or waves propagating through the material." Such properties can include, but are not limited to, conductivity, permittivity (i.e. dielectric), and magnetic permeability. The velocity of such fields or waves is determined from the travel time of the electromagnetic waves propagating through a volume or subvolume of the MUT and the known thickness of the MUT. A subvolume" is a part of the volume of the MUT through which the electromagnetic waves propogate. For convenience, this medium is referred to herein as a dielectric spacer, though in a more general sense, its magnetic properties may also vary. The dielectric characteristics and dimensions of the spacer are selected such that the calculated earliest arriving reflection from the bottom of the spacer precedes the diffraction from its outermost edges and precedes the arrival of a travel path including multiple reflections from the antenna-spacer bottom.

In some embodiments, a dielectric material is wrapped around the exterior surface of the MUT to minimize the interference of reflections from the outer walls of the MUT. In some embodiments, the measurement apparatus further includes a metal plate or other object of known electromagnetic properties that is placed on the side of the MUT distal to the antennas.

In some embodiments of use of the measurement apparatus for obtaining the bulk dielectric of the MUT, four measurements are made, including:

(1) a measurement with the antenna and dielectric spacer in free space or placed on a material with low conductivity, irrespective of the MUT;

(2) a measurement with a metal plate of known electromagnetic properties pressed against the bottom of the dielectric spacer;

(3) a measurement with the antenna and dielectric spacer pressed against a top surface of the MUT, while the opposing, bottom surface of the MUT is exposed to free space, or air; and (4) a measurement with the antenna and dielectric spacer pressed against the top surface of the MUT, while the opposing, bottom surface of the MUT is pressed against a metal plate having known electromagnetic properties.

Measurements (1) and (2) are calibration measurements, such that the subtraction of measurement (1) from measurement (2) provides an isolated reflection waveform used as a time reference indicative of the reflection arrival from the top surface of the MUT, or the bottom side of the dielectric spacer. Subtraction of measurement (3) from measurement (4) provides an isolated waveform representative of the reflection arrival time from the bottom surface of the MUT. Given the MUT thickness, and the difference between the reflection arrival times from the top and bottom surfaces of the MUT, the electromagnetic wave propagation velocity is calculated. The bulk dielectric of the MUT may be calculated from the propagation velocity using a known or approximately known magnetic permeability of the MUT.

In some embodiments, the bottom surface dielectric of the MUT can be derived by performing an additional measurement (5), in which the antenna and dielectric spacer are pressed against the top surface of the MUT, while the opposing, bottom surface of the MUT is pressed against another material having known dielectric properties. The subtraction of measurement (5) from measurement (4), provides an additional isolated reflection waveform. Given the amplitudes of the two isolated computed reflection waveforms, or the differences between waveforms obtained with three known dielectrics in contact with the bottom surface of the MUT (air in measurement 3, metal in measurement 4, and another material in measurement 5), the dielectric at the bottom surface of the MUT may be computed using Fresnel's equations.

In accordance with an embodiment of the disclosed technology, there is provided an apparatus for measuring the electromagnetic wave propagation velocity of a material under test (MUT) over a predefined area, the apparatus including an antenna assembly. The antenna assembly includes a transmitting antenna adapted to transmit energy, and a receiving antenna adapted to receive reflections, refractions, and diffractions of the transmitted energy. The transmitting antenna and the receiving antenna are separated by a separation distance. The antenna assembly is adapted to measure the electromagnetic propagation velocity within the MUT over the predefined area. The apparatus further includes a spacer with known electromagnetic properties, disposed directly beneath the antenna assembly. The spacer is adapted to slow propagation of waves, so as to prevent interference from signals arriving from edges of the predefined area and/or multiple reflections from one or more sides of the predefined area.

In some embodiments, the spacer is adapted to be in direct contact with an upper surface of the MUT. In some embodiments, the spacer includes a substantially homogenous substrate.

In some embodiments, the thickness of the spacer and dimensions of the spacer are selected based on a size of the predefined area.

In some embodiments, the predefined area includes a circular area of a cylindrical MUT. In such embodiments, the antenna assembly and the apparatus are adapted to substantially accurately measure at least one of the electromagnetic propagation velocity of the cylindrical MUT and the surface dielectric for a distal surface of the cylindrical MUT, which distal surface is distal to the spacer.

In some embodiments, the bulk dielectric of the MUT is calculated from the electromagnetic propagation velocity using known or approximately known magnetic properties of the MUT.

In accordance with another embodiment of the disclosed technology, there is provided a kit for measurement of the bulk dielectric of a Material Under Test (MUT) over a predefined area, the kit including an apparatus for measurement of the electromagnetic wave propagation velocity of a MUT as described herein. The kit further includes a first plate of a first material, having first electromagnetic properties, and a second plate of a second material, having second electromagnetic properties, the second electromagnetic properties being substantially different from the first electromagnetic properties.

In some embodiments, at least one of the first material and the second material is a metallic material.

In some embodiments, the kit further includes a third plate of a third material having third electromagnetic properties, substantially different from the first and second electromagnetic properties.

In some embodiments, the kit further includes a sleeve adapted to wrap around at least a portion of a perimeter of the MUT, the sleeve adapted to minimize the influence of reflected and refracted energy from sides of the MUT on reflections required for measurement of the bulk dielectric.

In some embodiments, a length of the sleeve is less than a thickness of the MUT. In some embodiments, the sleeve is formed of a material having electromagnetic properties which are substantially similar to electromagnetic properties of the MUT.

In accordance with yet another embodiment of the disclosed technology, there is provided a method for measuring a bulk dielectric of a material under test (MUT) over a predefined area, the MUT having a known thickness, a first surface, and a second, opposing surface, the method including using the apparatus described herein, obtaining a first measurement of the arrival time of reflections from a bottom surface of the spacer of the apparatus, the method further includes placing the apparatus above the first surface of the MUT in the predefined area and obtaining a second measurement of the arrival time of reflections from the second surface of the MUT. Subsequently, using the first and second measurements, computing a travel time of electromagnetic energy transmitted by the transmitting antenna of the apparatus through the MUT, and using the computed travel time, and the known thickness of the MUT, computing the bulk dielectric of the MUT.

In some embodiments, obtaining the first measurement includes obtaining a first waveform from a measurement of the antenna assembly of the apparatus conducted when the spacer is in free space or in contact with a dielectric material of known electromagnetic properties, and obtaining a second waveform from a measurement of the antenna assembly of the apparatus conducted when the spacer is placed on a material with substantially different electromagnetic properties than the dielectric material used for the first measurement. Subsequently, the first waveform is subtracted from the second waveform to obtain a third waveform and a reference point in time on the third waveform is identified as the first measurement.

In some embodiments, placing includes placing the spacer in direct contact with the first surface of the MUT.

In some embodiments, obtaining the second measurement includes obtaining a first waveform from a measurement of the antenna assembly of the apparatus conducted when the second surface of the MUT is in free space or in contact with a material of known electromagnetic properties, and obtaining a second waveform from a measurement of the antenna assembly of the apparatus conducted when the second surface of the MUT engages material with substantially different electromagnetic properties than the material used for the first measurement. Subsequently, the first waveform is subtracted from the second waveform to obtain a third waveform, and a reference point in time on the third waveform is identified as the second measurement.

In some embodiments, the MUT is a cylindrical MUT, and the predefined area includes a circular surface of the cylindrical MUT. In some such embodiments, the cylindrical MUT includes an asphalt core or a gyratory compacted asphalt sample.

In accordance with yet another embodiment of the disclosed technology, there is provided a method for measuring a surface dielectric of distal surface of a material under test (MUT) over a predefined area, the method including placing the apparatus described herein above a first surface of the MUT in the predefined area, the first surface being opposed to, and distal from, the distal surface of the MUT. Once the apparatus is placed, the method further includes obtaining a first waveform from a measurement of the antenna assembly of the apparatus conducted when the distal surface of the MUT engages a first material, obtaining a second waveform from a measurement of the antenna assembly of the apparatus conducted when the distal surface of the MUT engages a second material, and obtaining a third waveform from a measurement of the antenna assembly of the apparatus conducted when the distal surface of the MUT engages a third material. Once the waveforms are obtained, the first waveform is subtracted from the second waveform to obtain a first isolated reflection waveform, and the third waveform is subtracted from the second waveform to obtain a second isolated reflection waveform. The amplitudes of the first and second isolated reflection waveforms are used to compute the surface dielectric of the distal surface of the MUT based on Fresnel's equations. The electromagnetic properties of the first, second, and third materials are known and are substantially different from each other and from electromagnetic properties of the MUT.

In some embodiments, placing includes placing the spacer in direct contact with the first surface of the MUT.

In some embodiments, the MUT is a cylindrical MUT, and the predefined area includes a circular surface of the cylindrical MUT. In some such embodiments, the cylindrical MUT includes an asphalt core or gyratory-compacted asphalt sample.

Any device or step to a method described in this disclosure can comprise or consist of that which it is a part of, or the parts which make up the device or step. The term "and/or" is inclusive of the items which it joins linguistically and each item by itself.

DETAILED DESCRIPTION OF EMBODIMENTS OF THE DISCLOSED TECHNOLOGY

In an embodiment of the disclosed technology, a dielectric of a sample MUT is measured by averaging measurements over the sample, in a more accurate manner and for smaller sample sizes than is known in the art. This is accomplished by measuring reflection arrival times from a top surface of the MUT as well as from the bottom surface of the MUT. Based on the measured amount of time for radar to pass through the MUT and back, and a known thickness of the MUT, the dielectric is determined. In embodiments of the disclosed technology, the transmitting and receiving antennas of the apparatus are both on the same side of a dielectric spacer, and the MUT can be made of homogeneous or heterogeneous dielectric elements provided that the dimensions thereof are known.

Embodiments of the disclosed technology will become clearer in view of the following description of the drawings.

Figure 1A:
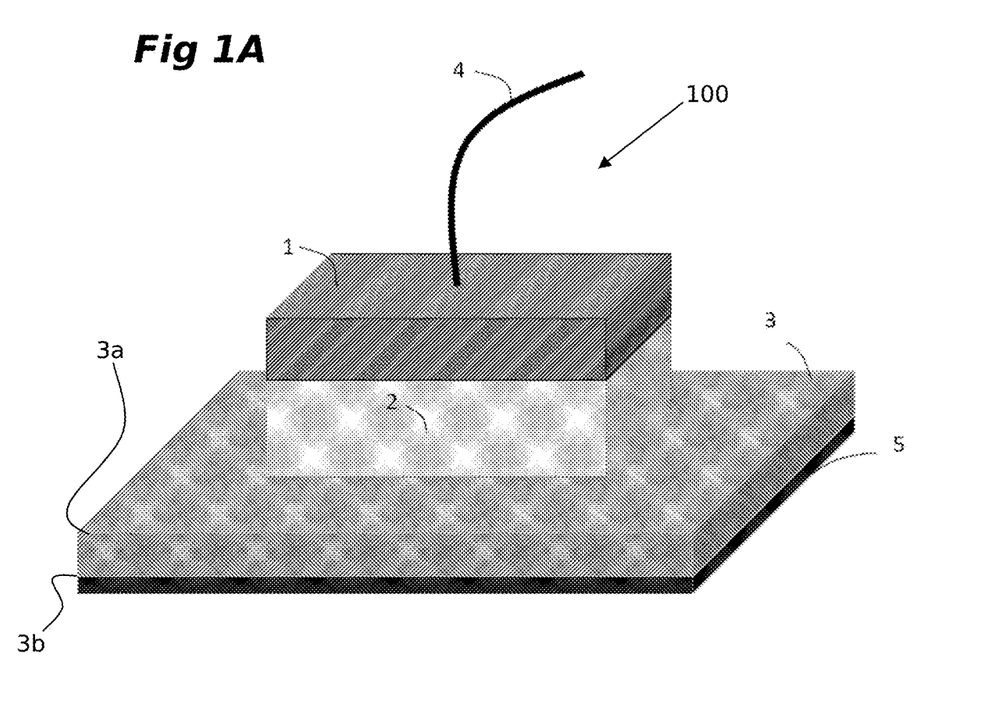
FIGS. 1A and 1B are perspective view illustrations of an apparatus for measuring a dielectric of a MUT according to an embodiment of the disclosed technology, the apparatus including a GPR antenna placed on top of the dielectric spacer which rests on the MUT, where the MUT rests on materials with known dielectric properties.
Figure 1B:
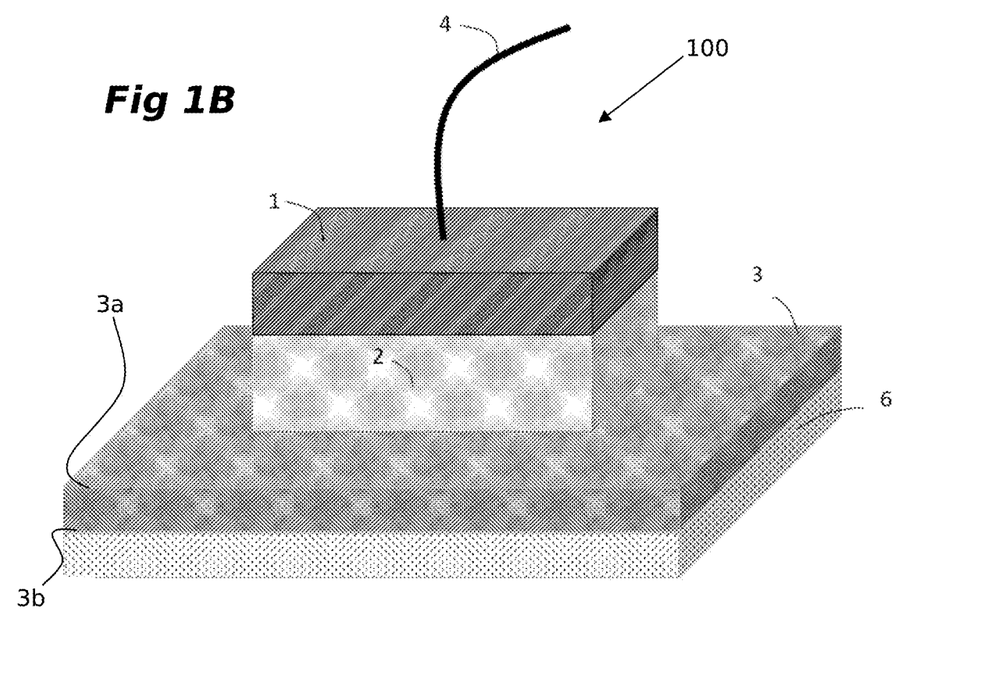

Reference is now made to FIG. 1, which are perspective view illustrations of an apparatus 100 for measuring a dielectric of a MUT 3 according to an embodiment of the disclosed technology. As seen in FIGS. 1A and 1B, a GPR (Ground Penetrating Radar) antenna 1 is disposed on top of a dielectric spacer 2, which is in direct contact with an upper surface 3a of the MUT 3. Measurement information may be transmitted to a control unit or another remote location via a communication cable 4 extending from GPR antenna 1.

The MUT 3 is place on top of a material with known approximate electromagnetic properties, such that a bottom surface 3b of MUT 3 engages the material. In FIG. 1A, the MUT 3 is disposed above a first material 5 having first known approximate electromagnetic properties, and in FIG. 1B, the MUT 3 is disposed above a second such material 6 having second known approximate electromagnetic properties. Typically, the properties of material 6 are substantially different from the properties of material 5.

In some embodiments, the dielectric spacer 2 is a substantially homogeneous substrate. In some embodiments, the dielectric spacer 2 has a higher dielectric than air, and sometimes has an estimated dielectric which is close to that of the medium being measured, thus causing slower propagation of waves there-through. In the context of the present application and claims, "close to" relates to two measurements being within 10%, within 20%, within 25% and/or within 30% of each other.

The apparatus 100 measures the dielectric over the surface area of the antenna 1. In some embodiments, the apparatus 100, and specifically antenna 1 and dielectric spacer 2, are designed to minimize the surface area over which the dielectric is measured.

One method of measuring the arrival time of reflection from the bottom surface 3b of the MUT 3, involves subtracting measurements made using the arrangement shown in FIG. 1A from measurements made using the arrangement shown in FIG. 1B. When the dielectric contrast between materials 5 and 6 is increased, so does the amplitude of the computed isolated reflection difference.

Figure 2A:
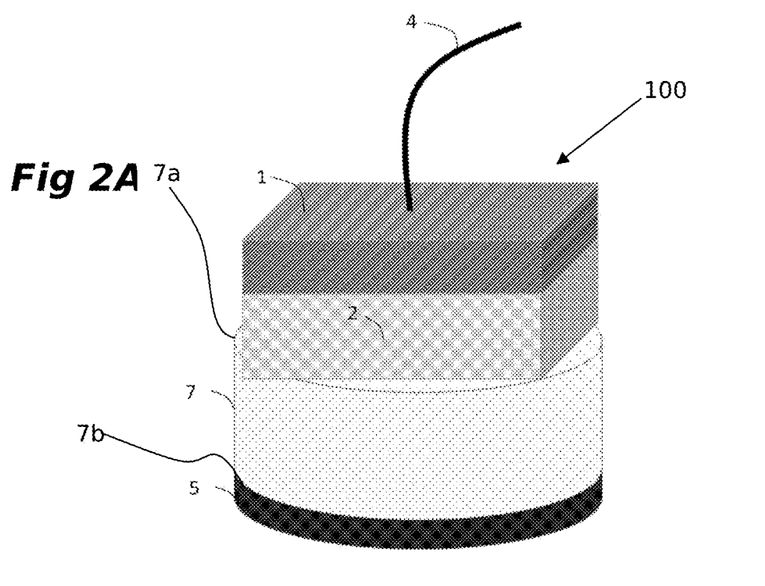
FIG. 2A is a perspective view illustration of the apparatus for measuring a dielectric of a MUT of FIGS. 1A and 1B, where the MUT is cylindrical and rests on materials with known electromagnetic properties.
Figure 2B:
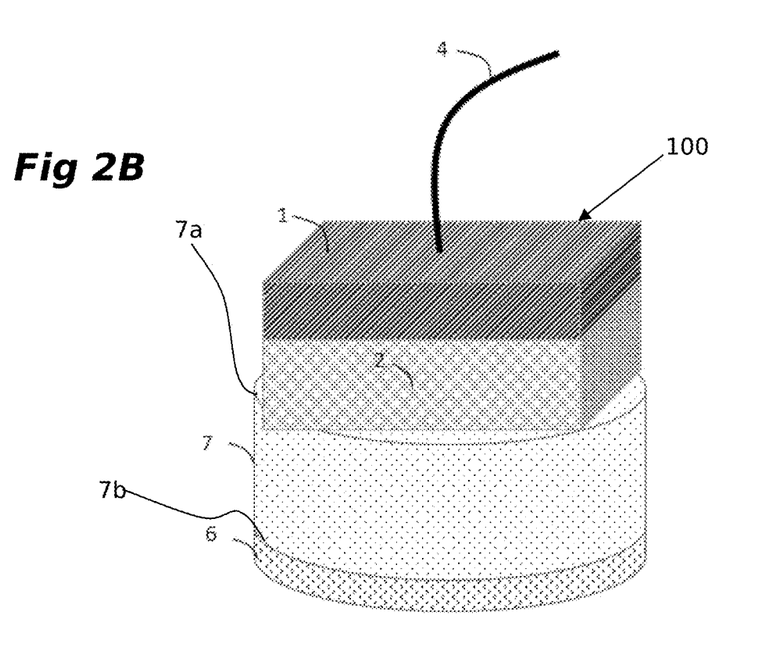
FIG. 2B is a further perspective view of the device shown in FIG. 2A.
Figure 2C:
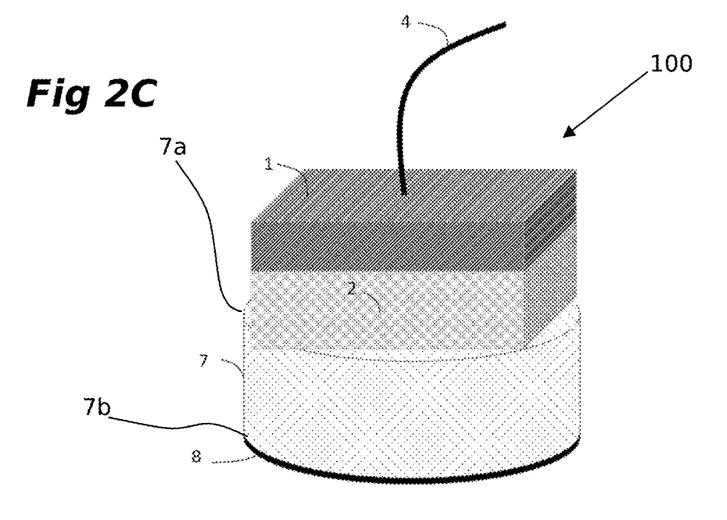
FIG. 2C is a further perspective view of the device shown in FIG. 2A.

FIGS. 2A, 2B, and 2C are perspective view illustrations of the apparatus 100, placed on top of a cylindrical MUT 7, according to an embodiment of the disclosed technology. The cylindrical MUT 7 includes upper surface 7a and bottom surface 7b, and may be of any suitable material, such as, for example, an asphalt core from a paved road, or a gyratory-compacted asphalt sample.

As seen, in FIG. 2A the MUT 7 is placed above a plate of material 5, as shown in FIG. 1A, and in FIG. 2B the MUT 7 is placed above a plate of material 6, as shown in FIG. 1B. In FIG. 2C, MUT 7 is placed above a third material 8 having third known approximate electromagnetic properties, different from the known properties of materials 5 and 6.

In some embodiments, a measurement is taken using the arrangement shown in FIG. 2C. In some embodiments, at least one material 5, 6, and 8 is metallic, so as to provide a substantially perfectly reflecting surface thereby to maximize the reflection difference when measurements are subtracted from one another.

While the bulk dielectric of the MUT 7 may be computed taking measurements using two different materials, such as in the arrangements shown in FIGS. 2A and 2B, three measurements using three different base materials are required in order to compute the surface dielectric of the bottom surface 7b of the MUT 7, as explained in further detail hereinbelow. As such, computation of the surface dielectric of surface 7b requires measurements using the arrangements of FIGS. 2A, 2B, and 2C. Similarly, if one were to try to compute the surface dielectric of surface 3b of FIGS. 1A and 1B, three measurements would be required.

Figure 3:
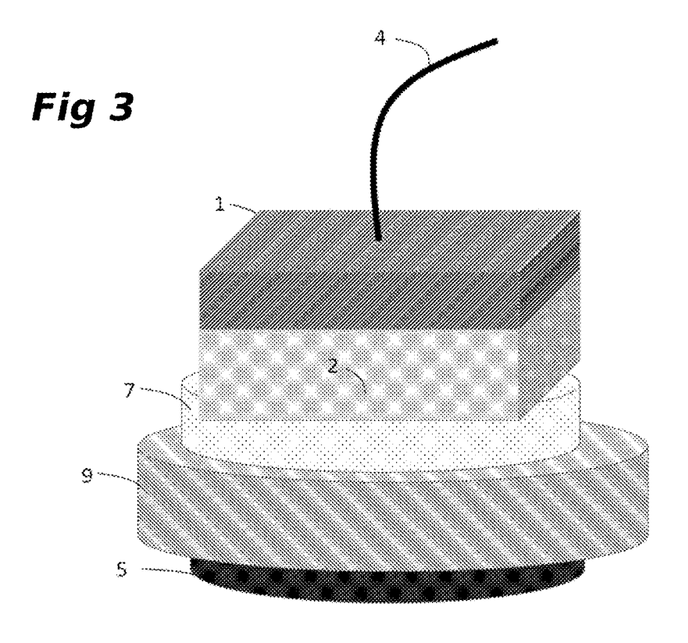
FIG. 3 is a perspective view illustration of the apparatus of FIG. 2A, where the MUT is enveloped by a sleeve according to an embodiment of the disclosed technology.

Reference is now made to FIG. 3, which is a perspective view illustration of apparatus 100 in an arrangement similar to that of FIG. 2A, where at least part of the MUT 7 is enveloped by a sleeve 9 according to an embodiment of the disclosed technology.

Sleeve 9 has approximately known electromagnetic properties, typically designed to be similar to the electromagnetic properties of the MUT 7. As seen, sleeve 9 envelopes the sides of the MUT 7, along at least a portion of the length of the MUT 7. In some embodiments, sleeve 9 may cover the entire length of the MUT. The purpose of sleeve 9 is to minimize the influence of the reflected and refracted energy received from sides of the MUT 7 on the reflection arriving from the center of the bottom surface 7b of the MUT. It will be appreciated that sleeve 9 may be used with any of the embodiments described herein, and is not limited only to the specific embodiment shown.

In some embodiments, and particularly for application involving measurement of a dielectric from a defined surface area, such as a cylinder, the electromagnetic properties of the dielectric spacer 2, and the dimensions of dielectric spacer 2, are selected such that the reflection which is the earliest to arrive at GPR antenna 1 from the surface area is minimally, or not at all, impacted by reflections and diffractions arriving at GPR antenna 1 from other travel paths.

Figure 4:
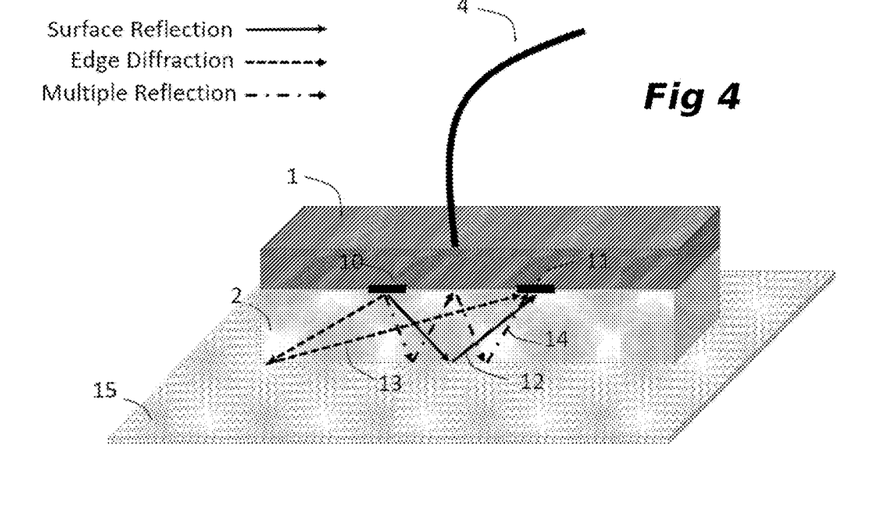
FIG. 4 is a cutaway perspective view of the apparatus of FIG. 1A including travel paths of radiated energy that are used for design calculations according to an embodiment of the disclosed technology.

FIG. 4 is a cutaway perspective view of the apparatus 100 of FIG. 1A, including travel paths of radiated energy that are used for calibration calculations according to an embodiment of the disclosed technology. As seen in FIG. 4, antenna 1 includes a transmitting antenna 10 and a receiving antenna 11. Surface reflection 12, edge diffraction 13, and multiple reflection 14 travel paths are shown in the Figure. A reflecting surface 15 shown in FIG. 4 may be a metal plate with length and width dimensions equal to or greater than those of spacer 2.

Knowledge of the separation distance between the transmitting antenna 10 and the receiving antenna 11, of the width of the transmit pulse used to obtain the reflection amplitude, and of the width, length, and thickness of spacer 2, enables the calculation of the arrival times of energy from the different paths for dielectric spacers 2 having different dimensions and dielectric properties. As such, the arrangement of FIG. 4 may be used to calibrate, or compute the optimal dimensions of dielectric spacer 2, which would minimize interference by reflections and edge diffractions.

Figure 5:
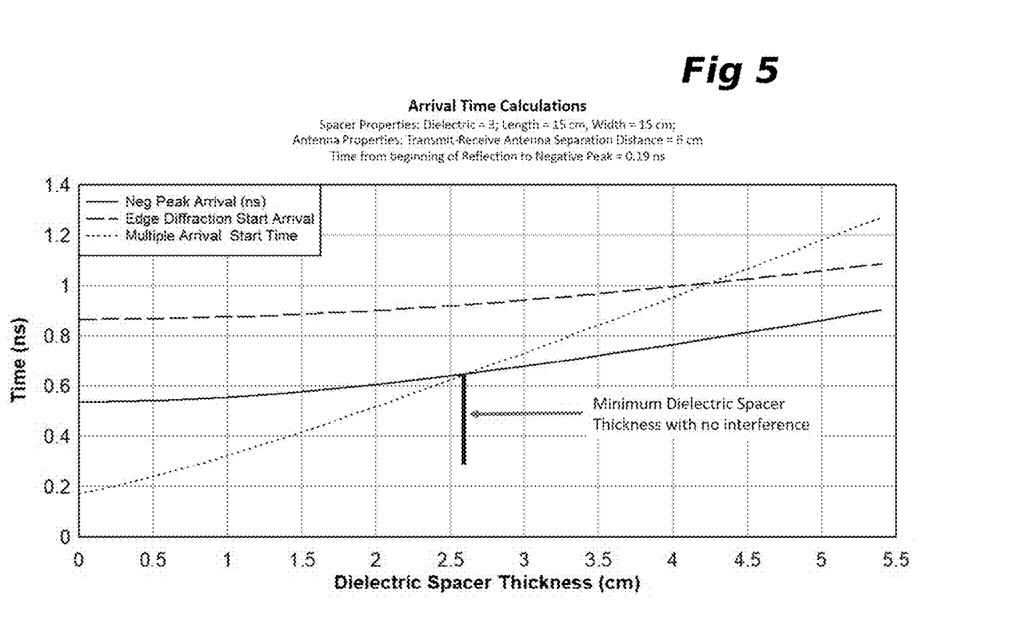
FIG. 5 is a graph demonstrating different reflection and diffraction arrival times calculated and used to determine the dielectric and dimensions of the dielectric spacer placed between the antennas and the MUT according to an embodiment of the disclosed technology.

An example of computation of such arrival times is provided in FIG. 5, which shows that for a spacer possessing a dielectric of 3.0, length and width of 15 cm, and a separation distance of 6 cm between the transmitting and receiving antennas, the minimum spacer thickness required to eliminate sensitivity to the multiple reflection is 2.6 cm.

Figure 6:
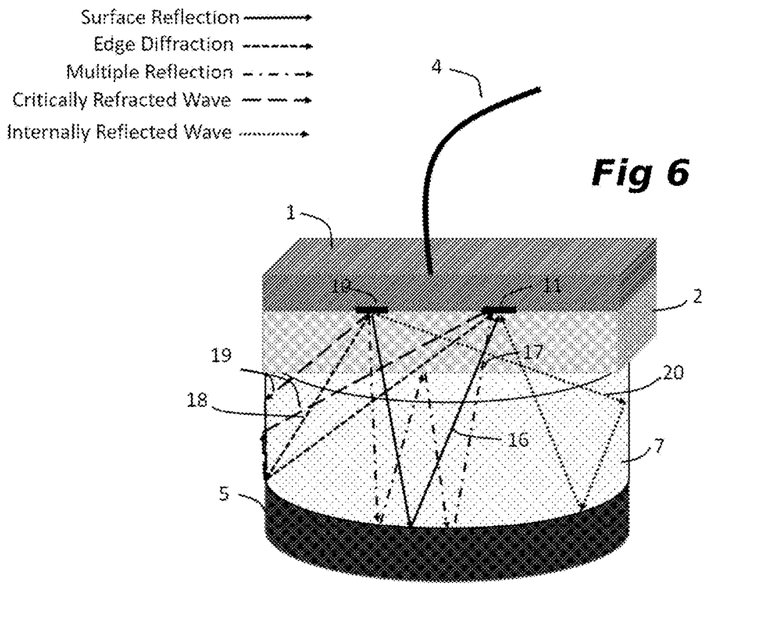
FIG. 6 is a cutaway perspective view illustration of the apparatus of FIG. 2A including travel paths of radiated energy according to an embodiment of the disclosed technology.

For MUTs with constrained dimensions, such as cylindrical MUTs as illustrated in FIGS. 2A to 3, there are numerous multi-path reflections, diffractions and refractions that may interfere with the desired reflection, which is the portion of the radiated wavefront impinging on the center of the bottom surface of the MUT. FIG. 6 is a cut-away perspective view illustration of the apparatus 100 of FIG. 2A, including of the antenna 1 and dielectric spacer 2 resting on top of cylindrical MUT 7 having upper surface 7a and bottom surface 7b, which in turn rests on top of material 5 with approximately known dielectric properties. The desired reflection 16 from the center of the bottom surface 7b of the MUT may potentially be impacted by a surface-to-bottom multiple reflection 17, diffraction 18 from an edge of the MUT, critically refracted energy 19 traveling along the circumferential surface of the cylindrical MUT, and an internal reflection 20 from the sides of the MUT. The impacts of all the different travel paths on the desired bottom reflection varies depending on the dimensions and the electromagnetic properties of the MUT.

Figure 7:
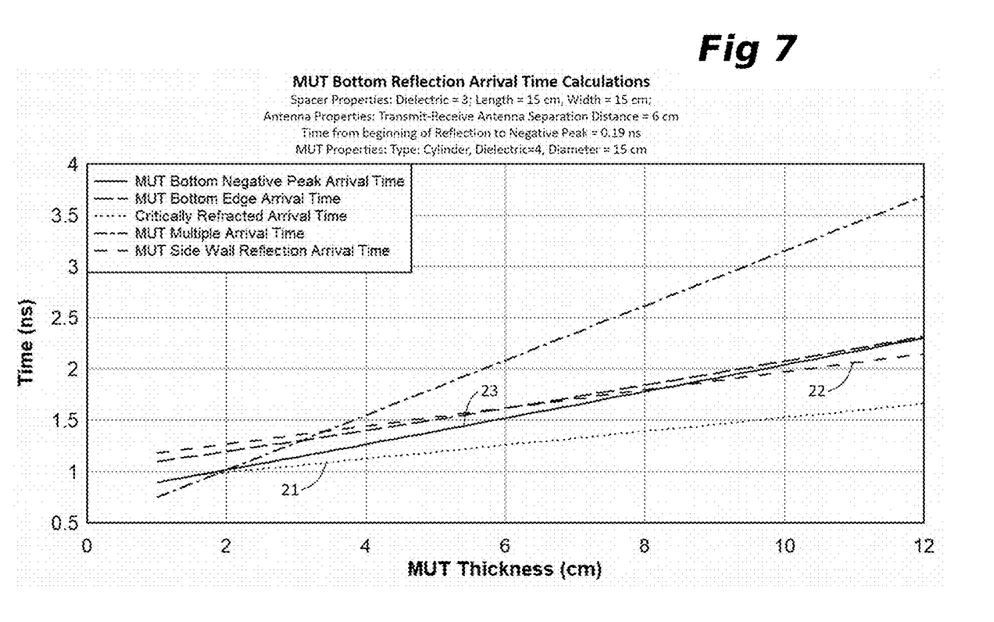
FIG. 7 is a graph demonstrating arrival times of reflections, diffractions, and refractions from the MUT as a function of the thickness of the MUT.

FIG. 7 is a graph demonstrating the calculated incipient arrival times of the different travel paths within the MUT for a cylindrical MUT 7 having a dielectric of 4, and diameter of 15 cm. The arrival times are shown as a function of the thickness of the MUT. As seen in FIG. 7, for a MUT having a diameter of 15 cm, at certain MUT thicknesses the critically-refracted energy 21 and MUT internal side wall reflection 22 interfere with the negative peak of the reflection 23 from the center of the bottom of the MUT. The extent of the interference varies and in some cases may be negligible. In other cases, a sleeve, such as sleeve 9 of FIG. 3, may be used to minimize the impact of travel paths involving the side wall of the MUT.

The apparatus 100 of the present invention can be used to accurately measure the travel time and/or amplitude of the portion of a radiated electromagnetic pulse that propagates through the MUT, is reflected off the bottom surface of the MUT, is received by a receiving antenna and is minimally impacted by multi-path reflections, diffractions and refractions. Knowledge of the thickness of the MUT permits the calculation of the bulk dielectric of the MUT from the reflection arrival time.

By making three separate measurements of the reflected pulse from the bottom surface of the MUT using different materials of known electromagnetic properties on which the MUT is placed, as illustrated in the arrangements of FIGS. 2A, 2B, and 2C, the dielectric of the MUT can be computed from the measured amplitudes of the reflections.

To aid in the understanding of a common intended use of the apparatus 100, the process of extracting the travel times and or amplitudes of the reflections is described herein. A calculation of the travel time through the MUT requires starting and ending time references. A convenient starting reference is the reflection from the bottom of the dielectric spacer 2.

Figure 8:
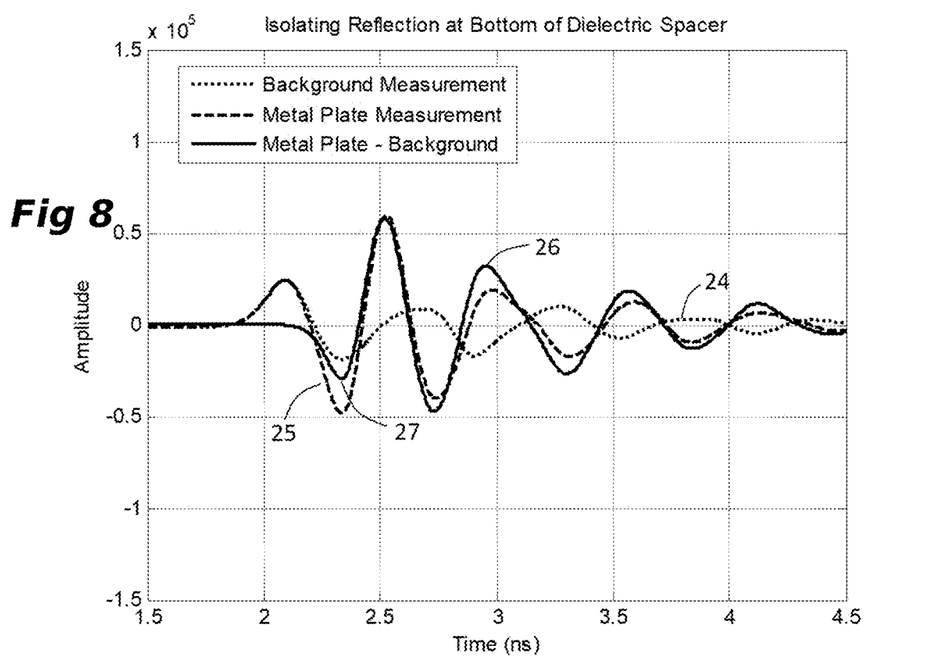
FIG. 8 is a graph demonstrating a method for isolating the arrival time from the bottom of the dielectric spacer according to an embodiment of the disclosed technology.

FIG. 8 shows a graph demonstrating a method for isolating the arrival time from the bottom of the dielectric spacer 2, or from the top surface of the MUT, according to an embodiment of the disclosed technology. Typically, this is a background measurement made with another dielectric material possessing the same dimensions and electromagnetic properties as a known sample placed under the dielectric spacer, for example as shown in FIG. 4. In general, the background measurement can be made with any material possessing electromagnetic properties such that the reflected energy is substantially different than those of metal. FIG. 8 shows a waveform 25 obtained from a measurement in which the dielectric spacer 2 is placed on a metal plate, as illustrated in FIG. 4, a waveform 24 representing a background measurement of reflections from the dielectric spacer when it is in free space, or placed on top of another dielectric material with similar or greater dimensions, and a waveform 26 representing the isolated reflection from the bottom surface of the dielectric spacer. The waveform 26 is obtained by subtracting the background measurement 24 from the measurement 25 using the metal plate measurement 25. The location of the first negative peak, here shown as peak 27, is the measurement point used as the arrival time of the reflection from the bottom of dielectric spacer 2. This arrival time, may then be used as a baseline arrival time, equivalent to the arrival time from the upper surface of a MUT disposed directly beneath dielectric spacer 2.

Figure 9:
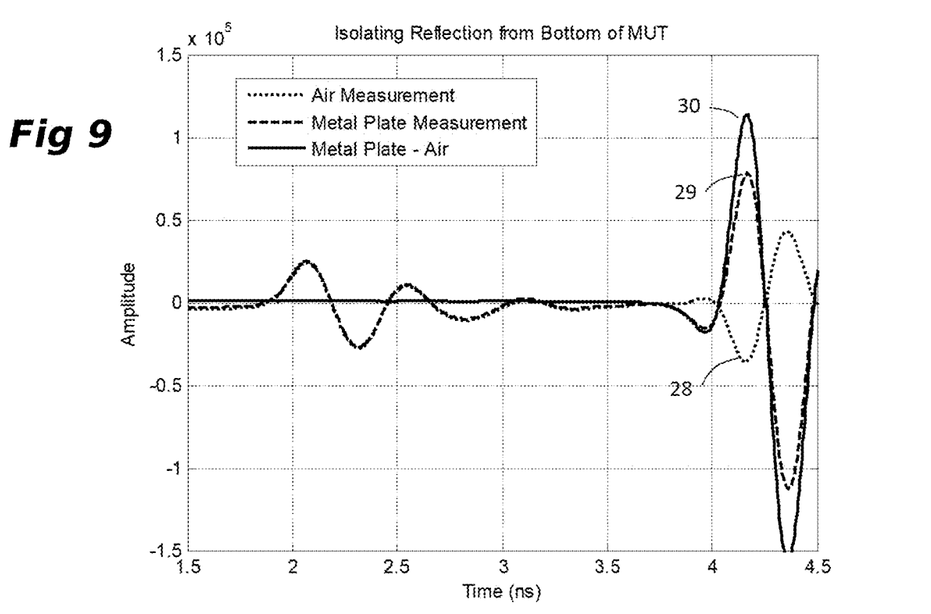
FIG. 9 is a graph demonstrating a method for isolating the arrival time from the bottom of the MUT according to an embodiment of the disclosed technology.

FIG. 9 is a graph demonstrating a method for isolating the arrival time from the bottom of the MUT according to an embodiment of the disclosed technology. Specifically, FIG. 9 represents the methodology of FIG. 8, when applied to reflections from the bottom of the MUT, rather than from the bottom of the dielectric spacer. In FIG. 9, one of the measurements is carried out when the MUT is in free space, or the bottom surface of the MUT engages air, whereas the other measurement is carried out when the MUT is placed on a metal plate. Subtracting the air measurement, represented by waveform 28, from the metal plate measurement, represented by waveform 29, isolates the arrival time 30 of the bottom reflection from the bottom surface of the MUT, as explained hereinabove with respect to FIG. 8.

Figure 10:
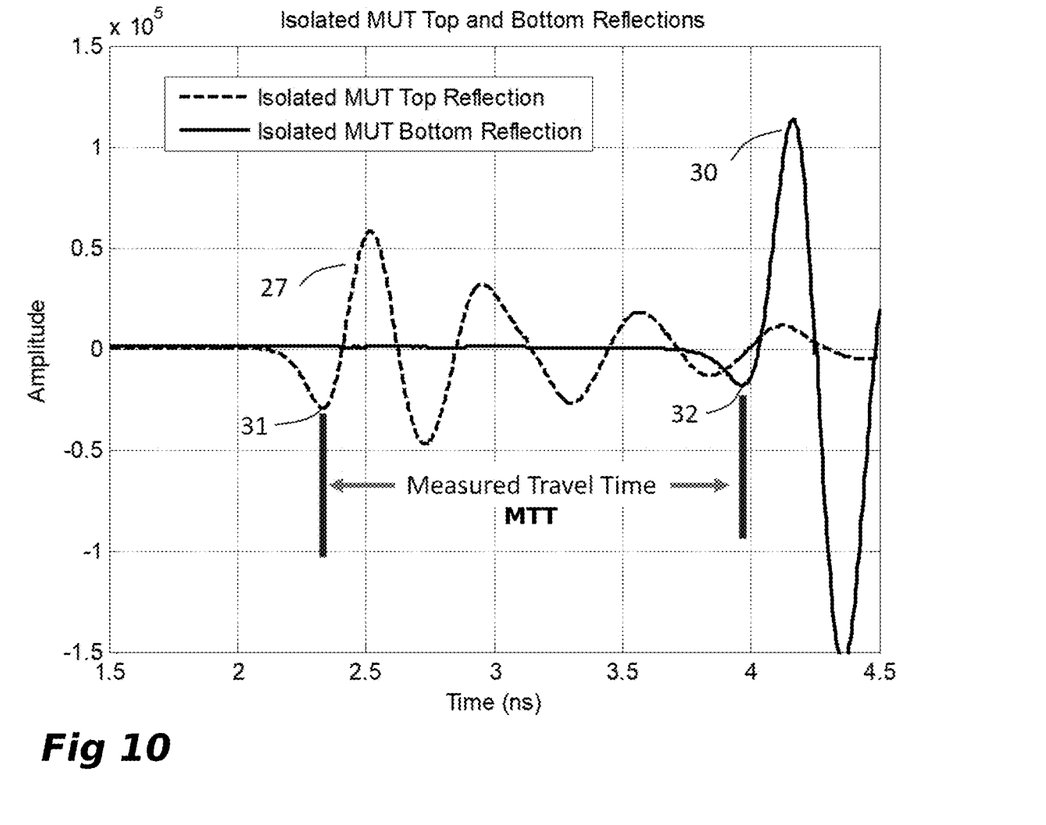
FIG. 10 is a graph demonstrating a method for obtaining the reflection travel time difference between the bottoms of the dielectric spacer and the MUT, to be used in calculation of the bulk dielectric of the MUT according to an embodiment of the disclosed technology.

FIG. 10 is a graph demonstrating a method for obtaining the reflection travel time difference between the bottoms of the dielectric spacer and the MUT, to be used in calculation of the bulk dielectric of the MUT according to an embodiment of the disclosed technology. As seen in FIG. 10, the waveform 31 of the reflection arrival time from the bottom surface of the dielectric spacer, computed using FIG. 8, and the waveform 32 of the reflection arrival time from the bottom surface of the MUT, computed using FIG. 9, are plotted on the same chart. The difference in the arrival times of the negative peaks of the reflection waveforms 31, 32 is used to calculate the travel time of the electromagnetic signal through the MUT, as indicated by MTT in FIG. 10.

Since the thickness of the MUT is known, once the travel time through the MUT is obtained using the computations of FIG. 10, the bulk dielectric of the MUT may be calculated using methods known in the art.

Apparatus 100 may also be used to compute a surface dielectric of the MUT, by utilizing the amplitudes of the isolated reflections differences obtained using the subtraction methodology of FIGS. 8 and 9. In this embodiment, a third measurement is made with a different dielectric material under the MUT, for example using the arrangement of FIG. 2C. The waveform representing the third measurement is subtracted from waveform 29 representing the metal plate measurement. The amplitudes corresponding to the two isolated reflection difference waveforms are used in a calculation based on Fresnel's equations to obtain the surface dielectric from the bottom surface 7b of the MUT (FIGS. 2A-2C), which faces away from the antenna 1 and dielectric spacer 2.

For purposes of this disclosure, the term "substantially" is defined as "at least 95% of" the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. An apparatus for measuring the electromagnetic wave propagation velocities of a subvolume or volume of a material under test (MUT), the apparatus comprising:
   an antenna assembly including a transmitting antenna adapted to transmit energy, and a receiving antenna adapted to receive reflections, refractions, and diffractions of said transmitted energy, said transmitting antenna and said receiving antenna being separated by a separation distance, said antenna assembly being adapted to measure the electromagnetic wave propagation velocity within the MUT over a predefined surface area; and
   a spacer with known electromagnetic properties, disposed in proximity or direct contact with said antenna assembly,
   wherein said spacer is adapted to slow propagation of waves, so as to prevent interference from signals arriving from edges of the predefined area and/or multiple reflections from one or more sides of the predefined area,
   are selected based on a size of the predefined area.

2. The apparatus of claim 1, wherein said spacer is adapted to be in close proximity to or direct contact with an upper surface of the MUT.

3. The apparatus of claim 1, wherein the thickness of said spacer and dimensions of said spacer are selected based on a size of the predefined area.

4. The apparatus of claim 1, wherein the predefined area comprises a circular area of a cylindrical MUT, and wherein said antenna assembly and said apparatus are adapted to substantially accurately measure at least one of the electromagnetic wave propagation velocity of said cylindrical MUT and the surface dielectric for a distal surface of said cylindrical MUT, which distal surface is distal to said spacer.

5. The apparatus of claim 1, wherein the bulk dielectric of the MUT is calculated from the electromagnetic wave propagation velocity using known or approximately known magnetic properties of the MUT.

6. A kit for measurement of the bulk dielectric of a Material Under Test (MUT) over a predefined area, the kit comprising:
   an apparatus for measurement of the electromagnetic wave propagation velocity of a MUT according to claim 1;
   a first plate of a first material, having first electromagnetic properties; and
   a second plate of a second material, having second electromagnetic properties, said second electromagnetic properties being substantially different from said first electromagnetic properties.

7. The kit of claim 6, wherein at least one of said first material and said second material is a metallic material.

8. The kit of claim 6, further including a third plate of a third material having third electromagnetic properties, substantially different from said first and second electromagnetic properties.

9. The kit of claim 6, further including a sleeve adapted to wrap around at least a portion of a perimeter of the MUT, said sleeve adapted to minimize the influence of reflected and refracted energy from sides of the MUT on reflections required for measurement of the bulk dielectric.

10. The kit of claim 9, wherein at least one of the following is true:
    a length of said sleeve is less than a thickness of the MUT; and
    said sleeve is formed of a material having electromagnetic properties which are substantially similar to electromagnetic properties of the MUT.

11. A method for measuring a bulk dielectric of a material under test (MUT) over a predefined area, the MUT having a known thickness, a first surface, and a second, opposing surface, the method comprising:
    using the apparatus of claim 1, obtaining a first measurement of the arrival time of reflections from a bottom surface of said spacer of said apparatus;
    placing said apparatus above the first surface of the MUT in the predefined area;
    obtaining a second measurement of the arrival time of reflections from the second surface of the MUT;
    using said first and second measurements, computing a travel time of electromagnetic energy transmitted by said transmitting antenna of said apparatus through the MUT; and
    using said computed travel time, and the known thickness of the MUT, computing the bulk dielectric of the MUT.

12. The method of claim 11, wherein said obtaining said first measurement comprises:
    obtaining a first waveform from a measurement of said antenna assembly of said apparatus conducted when said spacer is in free space or in contact with a dielectric material of known electromagnetic properties;
    obtaining a second waveform from a measurement of said antenna assembly of said apparatus conducted when said spacer is placed on a material with substantially different electromagnetic properties than said dielectric material used for said first measurement;
    subtracting said first waveform from said second waveform to obtain a third waveform; and
    identifying as said first measurement a reference point in time on said third waveform.

13. The method of claim 11, wherein said placing comprises placing said spacer in direct contact with the first surface of the MUT.

14. The method of claim 11, wherein said obtaining said second measurement comprises:
    obtaining a first waveform from a measurement of said antenna assembly of said apparatus conducted when the second surface of the MUT is in free space or in contact with a material of known electromagnetic properties;
    obtaining a second waveform from a measurement of said antenna assembly of said apparatus conducted when the second surface of the MUT engages material with substantially different electromagnetic properties than said material used for said first measurement;
    subtracting said first waveform from said second waveform to obtain a third waveform; and
    identifying as said second measurement a reference point in time on said third waveform.

15. The method of claim 11, wherein the MUT is a cylindrical MUT, and the predefined area comprises a circular surface of said cylindrical MUT.

16. The method of claim 15, wherein said cylindrical MUT comprises an asphalt core or a gyratory compacted asphalt sample.

17. A method for measuring a surface dielectric of distal surface of a material under test (MUT) over a predefined area, the method comprising:
    placing the apparatus of claim 1 above a first surface of the MUT in the predefined area, said first surface being opposed to, and distal from, the distal surface of the MUT;
    obtaining a first waveform from a measurement of said antenna assembly of said apparatus conducted when the distal surface of the MUT engages a first material;
    obtaining a second waveform from a measurement of said antenna assembly of said apparatus conducted when the distal surface of the MUT engages a second material;
    obtaining a third waveform from a measurement of said antenna assembly of said apparatus conducted when the distal surface of the MUT engages a third material;
    subtracting said first waveform from said second waveform to obtain a first isolated reflection waveform;
    subtracting said third waveform from said second waveform to obtain a second isolated reflection waveform;
    using amplitudes of said first and second isolated reflection waveforms, computing the surface dielectric of the distal surface of the MUT based on Fresnel's equations, wherein the electromagnetic properties of said first, second, and third materials are known and are substantially different from each other and from electromagnetic properties of the MUT.

18. The method of claim 17, wherein said placing comprises placing said spacer in direct contact with the first surface of the MUT.

19. The method of claim 17, wherein the MUT is a cylindrical MUT, and the predefined area comprises a circular surface of said cylindrical MUT.

20. The method of claim 19, wherein said cylindrical MUT comprises an asphalt core or gyratory-compacted asphalt sample.

* * * * *